(12) United States Patent
Wang et al.

(10) Patent No.: US 7,083,982 B2
(45) Date of Patent: Aug. 1, 2006

(54) HELIUM-NEON EXCITABLE RETICULOCYTE DYES DERIVABLE FROM HALOLEPIDINES

(75) Inventors: Nai-Yi Wang, Libertyville, IL (US); Alex W. C. Yem, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/288,139

(22) Filed: Nov. 5, 2002

(65) Prior Publication Data
US 2003/0145394 A1   Aug. 7, 2003

Related U.S. Application Data

(62) Division of application No. 08/763,022, filed on Dec. 10, 1996, now Pat. No. 6,495,692.

(51) Int. Cl.
*G01N 33/48* (2006.01)
*G01N 31/00* (2006.01)

(52) U.S. Cl. .................. 436/63; 436/52; 436/172; 436/800; 436/935; 435/7.1

(58) Field of Classification Search ............ 436/7.1, 436/935, 63, 172, 800, 52; 435/7.1
See application file for complete search history.

(56) References Cited

U.S. PATENT DOCUMENTS

| | | | |
|---|---|---|---|
| 3,157,507 A | 11/1964 | Bruengger et al. | 430/560 |
| 4,683,195 A | 7/1987 | Mullis et al. | 435/6 |
| 4,683,202 A | 7/1987 | Mullis | 435/91.2 |
| 4,883,867 A | 11/1989 | Lee et al. | 436/63 |
| 4,957,870 A * | 9/1990 | Lee et al. | 436/63 |
| 5,436,134 A | 7/1995 | Haugland et al. | 435/34 |
| 5,658,751 A | 8/1997 | Yue et al. | 435/34 |
| 6,368,864 B1 * | 4/2002 | Deka et al. | 436/10 |

FOREIGN PATENT DOCUMENTS

| | | |
|---|---|---|
| DE | 888046 | 8/1953 |
| EP | 0226272 | 6/1987 |
| EP | 0320308 | 6/1989 |
| EP | 0439182 | 7/1991 |
| FR | 1588846 | 4/1970 |
| JP | 1319743 | 12/1989 |
| WO | 9424213 | 10/1994 |
| WO | 9613552 | 5/1996 |

OTHER PUBLICATIONS

Search results "merck" "biotechters".*
Zhu, Thirty-Five Years of Studies on the Chemistry of Polymethane Cyanine Dyes, Dyes and Pigments, vol. 27, No. 2, pp. 77-111, 1995.
Netzel et al., Base-Content Dependence of Emission Enhancements, Quantum Yields, and Lifetimes for Cyanine Dyes bound to Double-Strand DNA: Photophysical Properties of Monomeric and Bichromophoric DNA Stains, Journal Physical Chemistry, 1995, 99, 17936-17947.

* cited by examiner

*Primary Examiner*—Celia Chang
(74) *Attorney, Agent, or Firm*—David L. Weinstein

(57) ABSTRACT

A method for synthesizing dyes excitable by a helium-neon laser (excitable at 633 nm) from hololepidines, e.g., 7-halolepidine, which dyes are suitable for detection and enumeration of reticulocytes in human blood samples. In another aspect, the invention provides a method for immunotyping phenocytes. The method is based on the phenomenon that when dyes of certain structure intercalate into DNA or RNA, the intensity of the dye increases. Dyes suitable for this invention can be described as having (a) a first heterocyclic moiety, (b) a second heterocyclic moiety, and (c) a linking group that connects the first and second heterocyclic moieties. Both the first and second heterocyclic moieties must contain at least two rings, preferably fused together. The dye is characterized by conjugation, whereby the first moiety is ethylenically conjugated to the second moiety.

10 Claims, No Drawings

HELIUM-NEON EXCITABLE RETICULOCYTE DYES DERIVABLE FROM HALOLEPIDINES

This application is a divisional of U.S. Ser. No. 08/763,022, filed Dec. 10, 1996 now U.S. Pat. No. 6,495,692.

BACKGROUND OF THE INVENTION

1. Field of the Invention

The present invention relates to dyes that are suitable for staining ribonucleic acid polymers (RNA) and deoxyribonucleic acid polymers (DNA) and are particularly suitable for staining reticulocytes. The invention further relates to a fluorescent composition.

2. Discussion of the Art

In many cases, there is a need to detect RNA or substances containing RNA. For example, a reticulocyte is a substance known to contain RNA. Detection of reticulocytes in a blood sample and the enumeration of these reticulocytes are valuable to clinicians. The reticulocyte count of a blood sample is an indicator of erythropoietic activity, is an indicator of acute hemorrhage and hemolytic anemia, and is a measure of response to iron, vitamin $B_{12}$, and folic acid therapy. As is known in the art, reticulocytes are precursors of mature red blood cells, and hence the term reticulocyte embraces the evolution and development of a mature red blood cell.

Detection and enumeration of reticulocytes in a blood sample have been carried out by both manual and automated methods by using appropriate stains such as new methylene blue (NMB), brilliant cresyl blue (BCB), acridine orange, and pyronin Y.

Vital staining with the dye new methylene blue is considered to be the reference method for reticulocyte determinations. In use, this dye precipitates RNA. The method is carried out manually and requires counting large numbers of cells with a microscope (for example, 500 to 1,000 cells). Consequently, the method is slow, tedious, and is subject to errors.

New methylene blue is nonfluorescent and true precipitated RNA is often difficult to differentiate from precipitated stain. New methylene blue stains by combining with intracellular RNA molecules to form a colored complex, which is visible under microscopic examination on account of its size and color. However, under certain conditions, the dye molecule itself can form complexes with other dye molecules. These dye/dye complexes are indistinguishable from dye/RNA complexes, with the possible result that counts are inaccurate and/or false positives for the specific cell type of interest are obtained. This problem is more likely when the dye solution has not been filtered to remove non-specific dye/dye complexes that have formed.

Acridine orange has been used for staining reticulocytes by both manual and automated procedures. Acridine orange, which is fluorescent, also precipitates RNA. Consequently, the use of this dye prevents quantitative estimates of RNA content because of potential quenching, a phenomenon caused by dye molecules interfering with one another in the energy transfer process. Under quenching conditions, the energy transfer process results in no net fluorescence emission.

Age profiles of cells based on RNA content being proportional to fluorescence are not reliable. Age profile is the key information sought to be derived in assays of blood cells. The function of the dye for staining reticulocytes is primarily to determine the percentage of immature red blood cells in the general circulation. The information is needed for determining the homeostasis of the blood cell formation, detection of blood cell related metabolic diseases, and the presence or absence of anemic diseases. Acridine orange has a great affinity for the plastic tubing in flow cytometers, thereby resulting in increased background, consequently requiring lengthy procedures for removing the dye from the flow cytometer tubing. In addition, cells stained by acridine orange are difficult to distinguish from the autofluorescent red cell peak. Finally, the reticulocyte count is usually lower than that obtained with new methylene blue. New methylene blue stains cells by combining with the intracellular RNA to form an insoluble precipitate within the cells. A discrete blue pattern is formed upon the interaction, thereby allowing for easy manual microscopic evaluation. Detection by means of acridine orange is performed on a flow cytometer. On account of the nature of the diffused pattern, it is difficult to differentiate the specific staining from acridine orange to that of non-specific background. Consequently, if the background is high, the net positive usually will be reduced and result in an artificially low value, compared with the more discrete new methylene blue staining method.

The use of pyronin Y requires prior fixation of the erythrocytes with formalin, is cumbersome, time consuming, and generally yields poor results. Moreover, pyronin Y has a very low quantum efficiency, leading to a very low fluorescent signals.

Accordingly, there is a need for providing a dye better suited for staining reticulocytes so as to provide a procedure for accurately determining reticulocytes in a blood sample.

A dye for staining reticulocytes preferably has the following properties:

1. The dye should not fluoresce in the absence of RNA.
2. The dye should have a good fluorescent quantum yield in the presence of RNA.
3. The dye must exhibit a certain level of water solubility and be able to penetrate the membrane of cells containing RNA.
4. The dye should preferably have an excitation peak at about 633 nm.

U.S. Pat. No. 4,957,870 involves the detection of reticulocytes, RNA, and DNA in human blood samples using a dye having the following structure:

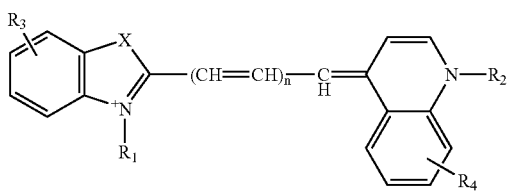

wherein
- X represents O, S, Se or $C(CH_3)_2$;
- $R_1$ represents an alkyl group having from 1 to 6 carbon atoms;
- $R_2$ represents an alkyl group having from 1 to 6 carbon atoms;
- $R_3$ represents fused benzene, alkyl group having from 1 to 6 carbon atoms, methoxy, or is absent;
- $R_4$ represents an alkyl group having from 1 to 6 carbon atoms, ethoxy, or is absent; and
- n represents zero or an integer from 1 to 6.

SUMMARY OF THE INVENTION

In one aspect, this invention provides a method for synthesizing dyes excitable by a helium-neon laser (excitable at 633 nm). The dyes are preferably derived from heterocyclic compounds, e.g., 7-halolepidine. The dyes are suitable for the detection and enumeration of reticulocytes in human blood samples. In another aspect, this invention provides a method for signal amplification. The method is based on the phenomenon that when dyes of certain structure intercalate into DNA or RNA, the intensity of the dyes increases.

Dyes suitable for this invention can be described as having (a) a first heterocyclic moiety, (b) a second heterocyclic moiety, and (c) a linking group that connects the first and second heterocyclic moieties. Both the first and second heterocyclic moieties must contain at least two rings, preferably fused together. The dye is characterized by conjugation whereby the first moiety is ethylenically conjugated to the second moiety.

The general structure of dyes suitable for use in this invention is shown below:

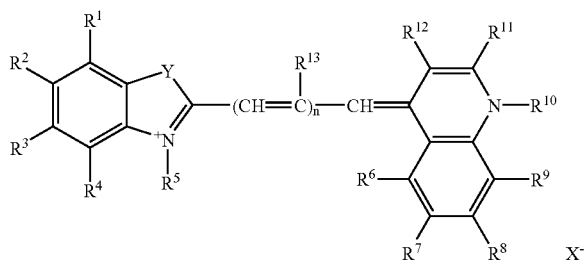

wherein:
$R^1$, $R^2$, $R^3$, $R^4$ independently represent a member selected from the group consisting of hydrogen, halogen, cyano, alkyl, aryl, alkaryl, aralkyl, or $R^1$ and $R^2$ taken together, or $R^2$ and $R^3$ taken together, or $R^3$ and $R^4$ taken together represent one or more rings;
$R^5$ represents an alkyl group or an aryl group;
$R^6$, $R^7$, $R^8$, $R^9$ independently represent a member selected from the group consisting of hydrogen, halogen, cyano, alkyl, aryl, alkaryl, aralkyl, or $R^6$ and $R^7$ taken together, or $R^7$ and $R^8$ taken together, or $R^8$ and $R^9$ taken together represent one or more rings, provided that at least one of $R^6$, $R^7$, $R^8$, $R^9$ represents halogen;
$R^{10}$ represents an alkyl group or an aryl group;
$R^{11}$, $R^{12}$ independently represent a member selected from the group consisting of hydrogen, halogen, cyano, alkyl, aryl, alkaryl, aralkyl, or $R^{11}$ and $R^{12}$ taken together represent one or more rings;
$R^{13}$ represents hydrogen or an alkyl group;
Y represents S, O, C, or Se, provided that Y is not N;
n represents a number from 0 to 3; and
$X^-$ represents a counter ion.

The ring of the first moiety that is attached to the linking group can be a five-membered or six-membered ring. The ring of the second moiety that is attached to the linking group can be a five-membered or six-membered ring.

$R^5$ and $R^{10}$ can be the same or different. Preferably, $R^5$ and $R^{10}$ represent an alkyl group having from 1 to 20 carbon atoms and from 0 to 6 heteroatoms, preferably from 1 to 10 carbon atoms and from 0 to 3 heteroatoms. $R^5$ and $R^{10}$ can be a straight chain, branched chain, or cyclic group. If $R^5$ of $R^{10}$ is an alkyl group, the carbon atoms of $R^5$ or $R^{10}$ can contain substitutents other than hydrogen atoms. $R^5$ and $R^{10}$ can also be (a) aryl groups, preferably having no more than five rings, more preferably no more than three rings, most preferably no more than one ring, or (b) alkenyl groups, preferably having from 2 to 20 carbon atoms, more preferably from 2 to 10 carbon atoms. If $R^5$ or $R^{10}$ is an aryl or an alkenyl group, the aryl or alkenyl groups of $R^5$ or $R^{10}$ can contain substitutents other than hydrogen atoms. $R^5$ and $R^{10}$ can be heteroaryl group groups, wherein heteroatoms can be selected from the group consisting of nitrogen, sulfur, oxygen, and selenium.

The identities of substituents for $R^5$ and $R^{10}$ are not critical, but they should be selected so as not to adversely affect the absorption characteristics of the dyes.

With respect to the value of n, there must be sufficient carbon atoms in the linking group to provide the desired absorption characteristics of the dye.

When $R^6$, $R^7$, $R^8$, or $R^9$ is a halogen, the halogen is preferably selected from the group consisting of F, Cl, and I.

If $R^1$, $R^2$, $R^3$, $R^4$, $R^6$, $R^7$, $R^8$, $R^9$, $R^{11}$, $R^{12}$, or $R^{13}$ is alkyl, it preferably contains 1 to 20, more preferably 1 to 10, and most preferably 1 to 6 carbon atoms. If $R^1$, $R^2$, $R^3$, $R^4$, $R^6$, $R^7$, $R^8$, $R^9$, $R^{11}$, $R^{12}$, or $R^{13}$ is aryl, it prefably contains no more than five rings, more preferably no more than three rings, and most preferably no more than one ring. If $R^1$, $R^2$, $R^3$, $R^4$, $R^6$, $R^7$, $R^8$, $R^9$, $R^{11}$, $R^{12}$, or $R^{13}$ is alkyl or aryl, it can contain substituents other than hydrogen. If $R^1$ and $R^2$ taken together, or $R^2$ and $R^3$ taken together, or $R^3$ and $R^4$ taken together, or $R^6$ and $R^7$ taken together, or $R^7$ and $R^8$ taken together, or $R^8$ and $R^9$ taken together, or $R^{11}$ and $R^{12}$ taken together form one or more rings, the rings can be aromatic or non-aromatic. The aromatic rings can be carbocyclic or heteroaromatic, wherein the hetroatoms are selected from the group consisting of nitrogen, sulfur, oxygen, and selenium. Preferably, ring structures formed by the foregoing combinations contain no more than five rings, preferably no more than three rings, and most preferably no more than one ring.

Dyes suitable for this invention exhibit very low background, narrow emission bands, and excellent enhancement when DNA or RNA is present. The dyes are stable to oxygen, moisture, and heat but are slowly decolored when exposed to light.

The dyes of this invention can be used as a signal generating agent for the detection of DNA or RNA. The dyes of this invention are sufficiently sensitive such that they can be used for the detection of reticulocytes in human blood samples on a flow cytometer using helium-neon (He—Ne) laser as the light source. Helium-neon lasers are much less expensive than argon lasers.

As mentioned previously, the dyes of this invention exhibit much higher enhancement, lower background, and smaller emission bandwidth than dyes used in the prior art. The low background and smaller emission bandwidth enables the dyes to be used for high resolution analyses of whole blood and in multiplexing assays.

DETAILED DESCRIPTION

Dyes suitable for this invention can be described as having a first heterocyclic moiety, a second heterocyclic moiety, and a linking group that connects the first and second heterocyclic moieties. Both the first and second heterocyclic moieties must contain at least two rings, preferably fused together. The dye is characterized by conjugation whereby the first moiety is ethylenically conjugated to the second moiety.

The general structure of dyes suitable for use in this invention is shown below:

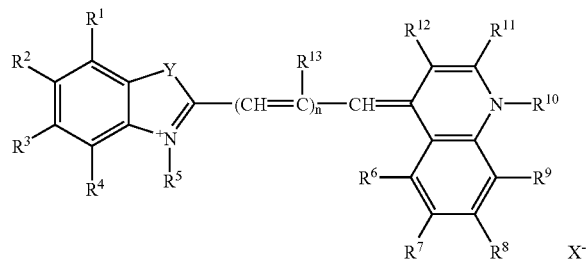

wherein:
$R^1$, $R^2$, $R^3$, $R^4$ independently represent a member selected from the group consisting of hydrogen, halogen, cyano, alkyl, aryl, alkaryl, aralkyl, or $R^1$ and $R^2$ taken together, or $R^2$ and $R^3$ taken together, or $R^3$ and $R^4$ taken together represent one or more rings;

$R^5$ represents an alkyl group or an aryl group;

$R^6$, $R^7$, $R^8$, $R^9$ independently represent a member selected from the group consisting of hydrogen, halogen, cyano, alkyl, aryl, alkaryl, aralkyl, or $R^6$ and $R^7$ taken together, or $R^7$ and $R^8$ taken together, or $R^8$ and $R^9$ taken together represent one or more rings, provided that at least one of $R^6$, $R^7$, $R^8$, $R^9$ represents halogen;

$R^{10}$ represents an alkyl group or an aryl group;

$R^{11}$, $R^{12}$ independently represent a member selected from the group consisting of hydrogen, halogen, cyano, alkyl, aryl, alkaryl, aralkyl, or $R^{11}$ and $R^{12}$ taken together represent one or more rings;

$R^{13}$ represents hydrogen or an alkyl group;

Y represents S, O, C, or Se, provided that Y is not N;

n represents a number from 0 to 3; and $X^-$ represents a counter ion.

The ring of the first moiety that is attached to the linking group can be a five-membered or six-membered ring. The ring of the second moiety that is attached to the linking group can be a five-membered or six-membered ring.

$R^5$ and $R^{10}$ can be the same or different. Preferably, $R^5$ and $R^{10}$ represent an alkyl group having from 1 to 20 carbon atoms and from 0 to 6 heteroatoms, preferably from 1 to 10 carbon atoms and from 0 to 3 heteroatoms. $R^5$ and $R^{10}$ can be a straight chain, branched chain, or cyclic group. The alkyl groups of $R^5$ and $R^{10}$ can contain substitutents other than hydrogen atoms. $R^5$ and $R^{10}$ can also be (a) aryl groups, preferably having no more than five rings, more preferably no more than three rings, most preferably no more than one ring, or (b) alkenyl groups, preferably having from 2 to 20 carbon atoms, preferably from 2 to 10 carbon atoms. The aryl or alkenyl groups of $R^5$ and $R^{10}$ can contain substitutents other than hydrogen atoms.

The identities of substituents for $R^5$ and $R^{10}$ are not critical, but they should be selected so as not to adversely affect the absorption characteristics of the dyes.

$R^5$ and $R^{10}$ can be heteroaryl group groups, wherein heteroatoms can be selected from the group consisting of nitrogen, sulfur, oxygen, and selenium.

With respect to the value of n, there must be enough carbon atoms in the linking group to provide the desired absorption characteristics of the dye.

When $R^6$, $R^7$, $R^8$, or $R^9$ is a halogen, the halogen is preferably selected from the group consisting of F, Cl, and I.

If $R^1$, $R^2$, $R^3$, $R^4$, $R^6$, $R^7$, $R^8$, $R^9$, $R^{11}$, $R^{12}$, or $R^{13}$ is alkyl, it preferably contains 1 to 20, more preferably 1 to 10, and most preferably 1 to 6 carbon atoms. If $R^1$, $R^2$, $R^3$, $R^4$, $R^6$, $R^7$, $R^8$, $R^9$, $R^{11}$, $R^{12}$, or $R^{13}$ is aryl, it preferably contains no more than five rings, more preferably no more than three rings, and most preferably no more than one ring. If $R^1$, $R^2$, $R^3$, $R^4$, $R^6$, $R^7$, $R^8$, $R^9$, $R^{11}$, $R^{12}$, or $R^{13}$ is alkyl or aryl, it can contain substituents other than hydrogen. If $R^1$ and $R^2$ taken together, or $R^2$ and $R^3$ taken together, or $R^3$ and $R^4$ taken together, or $R^6$ and $R^7$ taken together, or $R^7$ and $R^8$ taken together, or $R^8$ and $R^9$ taken together, or $R^{11}$ and $R^{12}$ taken together form one or more rings, the rings can be aromatic or non-aromatic. The aromatic rings can be carbocyclic or heteroaromatic, wherein the hetroatoms are selected from the group consisting of nitrogen, sulfur, oxygen, and selenium. Preferably, ring structures formed by the foregoing combinations contain no more than five rings, preferably no more than three rings, and most preferably no more than one ring.

$X^-$ represents a counter ion, preferably acetate.

The dyes are preferably soluble in water and stable under conditions of use, such as, for example, in a flow cytometer. The dyes are capable of being linked to a molecule, e.g., a protein or a polymer, through the moiety $R^5$, the moiety $R^{10}$, or another moiety.

When not bound to a nucleic acid, the dyes of the invention exhibit a strong absorption peak in the range of from about 600 nm to about 630 nm; however, in the unbound state, the dye does not provide either a detectable excitation or emission peak. When the dyes stain the RNA in the reticulocytes, the optical properties of the dye change dramatically. In particular, the absorption curve shifts to a longer wavelength, and the dye exhibits strong fluorescence. For a typical dye useful in this invention, the excitation maximum is at about 633 nm, and the emission maximum is at about 670 nm, giving a Stokes shift of about 40 nm. As a result of the excitation peak of the bound dye being in the order of about 633 nm, the light source for use with the automatic flow cytometer may be a helium-neon laser, which has strong emission at 633 nm. The lack of fluorescence of the dye when not bound to nucleic acid provides low backgrounds and allows an operator to select a fluorescent threshold (or "gate") for a flow cytometer by simply running an unstained control. Although excitation may be effected at other wavelengths, the reticulocytes stained with the dyes described herein are preferably excited at a wavelength of from about 630 nm to about 670 nm. Representative examples of dyes suitable for use in this invention have the following structural formulas. In the following structures, "Ph" represents the phenyl group, "Ar" represents an aryl group, a single straight line represents —$CH_3$, and a broken line represents —$CH_2CH_3$.

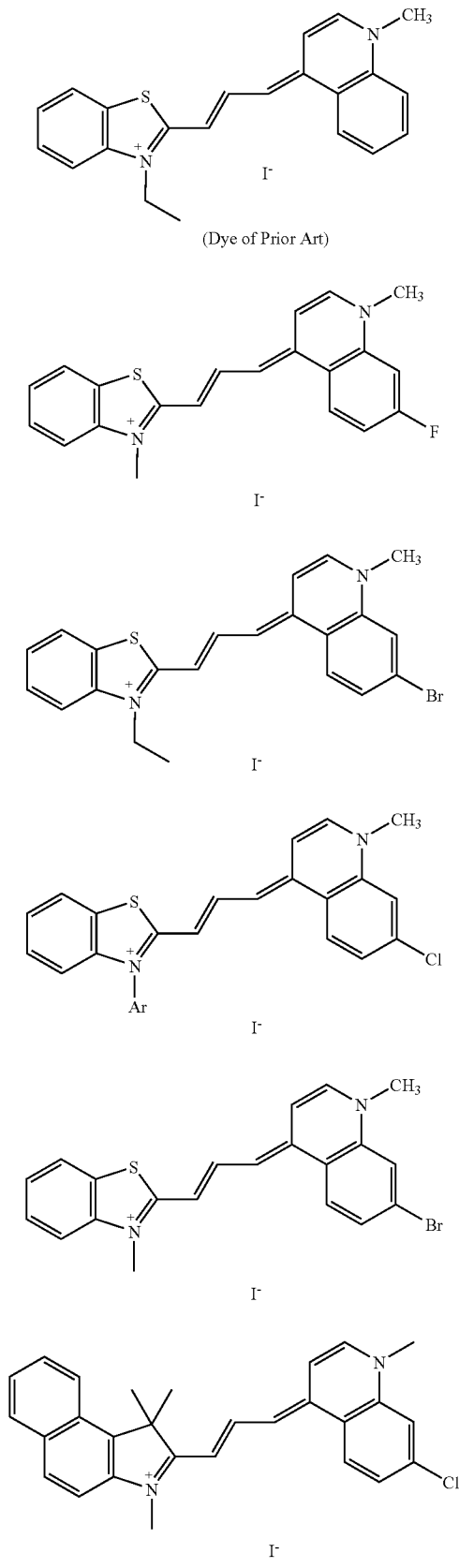

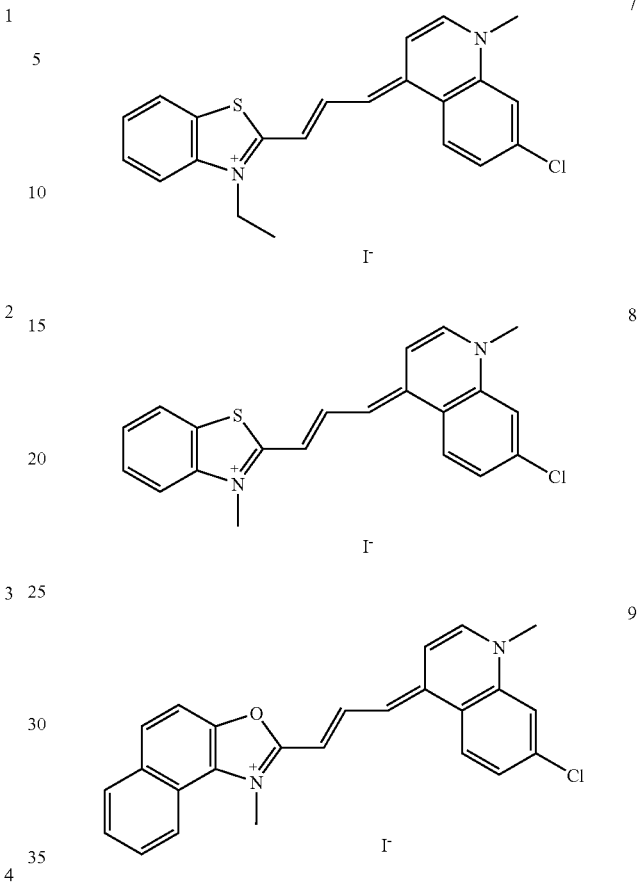

The following table sets forth the absorption maximum in nanometers for several dyes suitable for use in this invention.

TABLE I

| Dye number | Absorption maximum (nm) |
| --- | --- |
| 2 | 628 |
| 5 | 638 |
| 6 | 632 |
| 7 | 638 |
| 8 | 638 |
| 9 | 624 |

Dyes suitable for use in this invention can be prepared by
(1) reacting a heterocyclic compound containing at least two fused rings with acetic anhydride and N,N'-diphenylformamidine or its higher homologs to form a chain-extended intermediate;
(2) reacting the aforementioned chain-extended intermediate with a methylated halolepidine in the presence of a tertiary alkyl amine catalyst under reflux conditions to form the dye.

The resultant dye can then be recovered by precipitation, typically by diethylether. Alternatively, dyes suitable for this invention can be prapred by
(1) reacting a heterocyclic compound containing at least two fused rings and an activated methyl group with acetic anhydride and N,N'-diphenylformamidine or its higher homologs to form a chain-extended intermediate;

(2) reacting the aforementioned chain-extended intermediate with a halolepidine in the presence of a tertiary alkyl amine catalyst under reflux conditions to form the dye.

The resultant dye can then be recovered by precipitation, typically by diethylether.

Representative examples of compounds containing at least two fused rings include 2-methyl-N-alkyl benzothiazolium iodide, 2-methyl-N-alkyl benzoxazolium iodide, 2-methyl-N-alkyl naphthoxazolium iodide, and 2-methyl-N-alkyl napthothiazolium iodide. Representative examples of N-methylated halolepidines includes 7-chlorolepidine, 7-fluorolepidine, and 7-bromolepidine.

Dyes suitable for use in this invention can be prepared according to the following scheme of synthesis. In the following scheme of synthesis, "Ph" represents the phenyl group and "Ac" represents the acyl group, and "X" represents the halo group.

TABLE II-continued

| Dye | R | X |
|-----|---|---|
| 7 | —CH$_2$CH$_3$ | —Cl |
| 8 | —CH$_2$CH$_3$ | —Cl |
| 9 | —CH$_3$ | —Cl |

In accordance with the present invention, the dyes of the invention may be employed in the form of an aqueous solution when staining reticulocytes in a blood sample, and, in particular, in the form of an isotonic saline solution. The saline solution may contain a minor amount of methanol. The blood sample, which may be whole blood or a blood fraction, is stained with the dye by mixing the blood sample with the solution comprising the dye. It has been found that

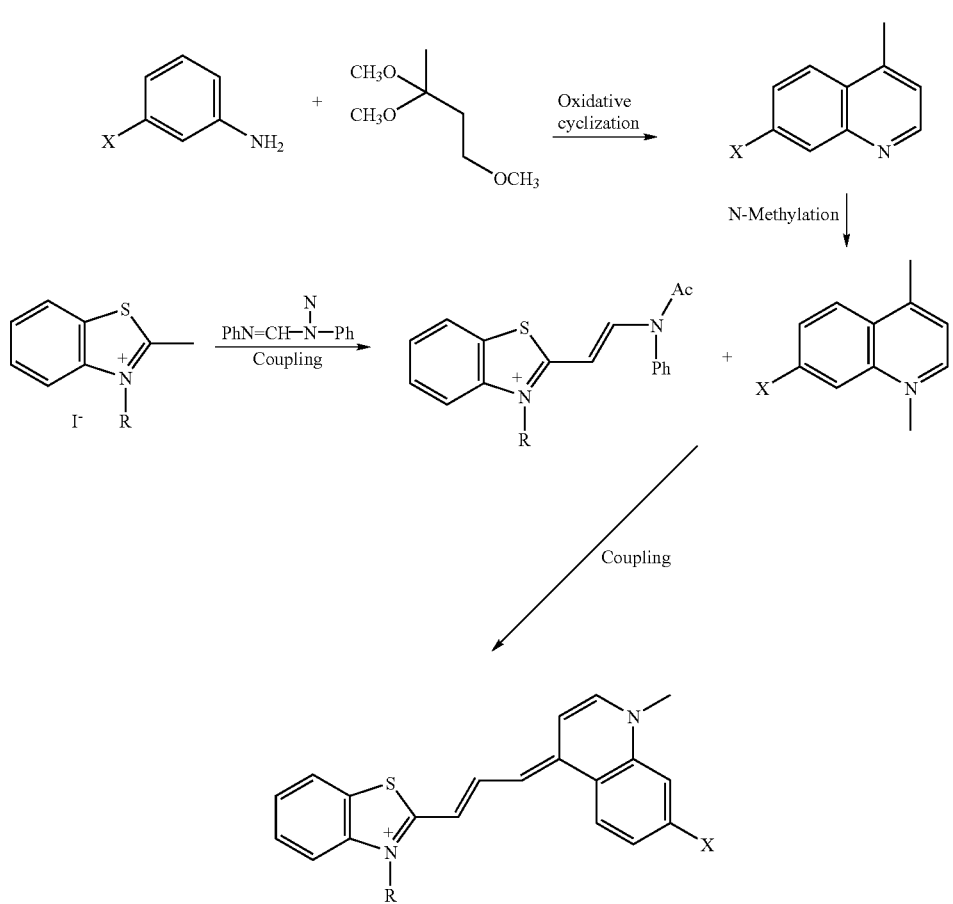

In the foregoing scheme of synthesis, representative sets of the substituents R and X include the following:

TABLE II

| Dye | R | X |
|-----|---|---|
| 2 | —CH$_3$ | —F |
| 5 | —CH$_3$ | —Br |
| 6 | —CH$_3$ | —Cl | by using the dyes described herein as the staining medium, it is possible to detect and enumerate reticulocytes in a whole blood sample.

Because the dye must permeate the reticulocyte, it should have excellent cell-permeation properties. The dyes suitable for this invention do not precipitate RNA, and as a result, the stained reticulocyte cells maintain a relatively homogeneous distribution of intracellular RNA, whereby it is possible to designate a threshold value demarcating the distinction between a reticulocyte and a mature red cell. This characteristic provides the physician with additional information beyond the reticulocyte count in that RNA content is a function of the age of the reticulocytes. Accordingly, by using a dye described herein, a clinician has the ability to perform reticulocyte age profiles as well as simple reticulocyte counts. The use of dyes described herein for staining reticulocytes in a blood sample offers the further advantage that the fluorescent signals from the stained reticulocytes are readily distinguishable from those of the mature erythrocytes, which contain no RNA or DNA. For this reason, results can be directly read in a flow cytometer without extensive data manipulation.

Although reticulocytes and RNA or DNA stained with a dye of the invention are preferably enumerated in an automatic flow cytometer, they can also be counted by a manual procedure or automated microscopy.

The present invention is not limited to the use of any particular flow cytometer. Thus, for example, stained reticulocytes may be detected and enumerated in an automated flow cytometer or a semi-automated flow cytometer or a manual flow cytometer. In using automated flow cytometers, fluorescent gates are set by use of an unstained control sample, and the fluorescent gates are then used on the stained sample.

The dyes described herein can be used directly to stain reticulocytes. They need not be attached to an antibody or the like to form a conjugate. Staining can be brought about by an intercalation mechanism, whereby intercalation of the dye with RNA or DNA of the reticulocyte causes a blue shift or a red shift in excitation or emission wavelength.

Alternatively, the dyes described herein can be used in the form of a conjugate. One application of using a conjugate comprising a dye described herein is in a flow cytometry application that employs a fluorescent conjugate or multiple fluorescent conjugates to detect cells contained in a test sample. An example of a flow cytometer is the Fluorescence Activated Cell Sorter (FACScan) manufactured by Becton, Dickinson & Co, Franklin Lakes, N.J. In general, an imaging system contains an excitation source and a detection device. The excitation source excites the fluorescent signal generating group associated with the conjugate and the detection device detects the signal emitted from the excited signal generating group.

In a typical imaging system analysis, a test sample is incubated with a fluorescent conjugate, which specifically binds certain cells that may be present in the test sample. The incubation takes place for a time and at a temperature conducive for the binding of the conjugate to specific cell populations contained in the sample. The cells bound with the conjugate are commonly referred to as being stained and the staining procedure can be executed multiple times, sequentially or at the same time, with multiple conjugates, which emit signals of varying wavelengths. After the staining procedure is complete, the sample can be analyzed using a flow cytometer.

In an alternative embodiment, a conjugate comprising the dyes described herein can be adapted for use in conventional solid phase immunoassays such as, for example, a sandwich type immunoassay. A sandwich type immunoassay typically involves contacting a test sample suspected of containing an analyte with a substantially solid inert plastic, latex or glass bead or microparticle, or other support material which has been coated with a specific binding member that forms a binding pair with the analyte. The binding member-coated support material is commonly referred to as a "capture reagent". After the analyte is bound to the support material, the remaining test sample is removed from the support material. The support material, to which the analyte is bound, is treated with a conjugate, which generally comprises a second binding member labeled with a signal-generating group. The conjugate becomes bound to the analyte, which is bound to the support material. The combination of support material having the first binding member, the analyte, and the conjugate bound thereon is separated from any unbound conjugate, typically with one or more wash steps. The signal generated by the signal generating group, through appropriate excitation, can then be observed visually, or more preferably by an instrument, to indicate the presence or amount of an analyte in a test sample. It will be understood, of course, that the order and number of the steps employed to perform such assays are not intended to limit the invention described herein.

The analyte detected by such an immunoassay can be the product or products of an amplification reaction. Accordingly, the analytes can comprise nucleic acid sequences or can be otherwise the products of a hybridization reaction such as LCR, which is described in European Patent Applications EP-A-320 308 and EP-A-439 182, and PCR, which is described in U.S. Pat. Nos. 4,683,202 and 4,683,195, all of which are incorporated herein by reference. In cases where the analytes comprise, for example, LCR or PCR reaction products or sequences, the sequences can comprise or be modified to comprise a binding member that forms a binding pair with an indicator reagent and a binding member that forms a binding pair with a capture reagent.

The use of reticulocytes stained with the dyes described herein in a flow cytometer is particularly advantageous in that there are low fluorescent backgrounds, and fluorescent gates may be easily selected by use of an unstained control. Moreover, because there is no precipitation of intracellular reticulocyte RNA, whereby the cells need not be fixed. In addition, the relationship between the fluorescent signal and the individual reticulocytes provides information as to the age of the reticulocytes.

Still another advantage of the prevent invention is that reticulocytes stained with the dyes descibed herein can be used in an automated flow cytometer having lower light intensity, e.g., one may use a helium-neon laser as opposed to an argon laser.

The following examples illustrate various features of the present invention but is not intended to in any way limit the scope of the invention as set forth in the claims.

EXAMPLE I

Preparation of 7-chlorolepidine

To a mixture containing 3-chloroaniline (1.59 g), ferric chloride hexahydrate (5.4 g), zinc chloride (0.2 g), ethanol (20 ml of 95% aqueous solution) preheated to 60° C. was added 1,3,3-trimethoxybutane (1.48 g). The resulting mixture was refluxed for two hours and allowed to stand overnight. The volatile matrials were then removed in vacuo and the residue rendered basic with 10% aqueous sodium hydroxide. The resulting mixture was partitioned between water and diethyl ether (3 times). The combined ether layer was dried over magnesium sulfate. Rotary evaporation of the ether solution gave a dark liquid. The liquid was added to a silica gel column and eluted with hexane/ethyl acetate (3:1) to give the desired product as tan crystals.

Preparation of 7-chloro-1-methyllepidinium iodide

A portion of the 7-chlorolepidine (80 mg) prepared as above was methylated by heating with $CH_3I$ (0.5 ml) in $CH_3CN$ (1 ml) at reflux for two hours. The mixture was treated with diethyl ether, followed by centrifugation, to give a yellow powder.

Activation of 3-ethyl-2-methylbenzothiazolium iodide

A mixture of 3-ethyl-2-methylbenzothiazolium iodide (350 mg) and N,N'-diphenylformamidine (420 mg) in acetic anhydride (10 ml) was heated to 120° C. for 30 minutes. Diethyl ether was added and the suspension was centrifuged. The supernatant was decanted and the precipitate washed with more diethyl ether and dried.

Preparation of Dye 7

To the activated 3-ethyl-2-methylbenzothiazolium derivative obtained above (4.5 mg) was added the 7-chloro-1-methyllepidinium salt obtained above (3.8 mg) in chloroform (250 μL) to form a mixture. Then triethylamine (50 μL) was added to the mixture. The resulting mixture was stirred at reflux for 30 minutes, during which time a dark blue solution was obtained. Diethyl ether was added to the solution and the resultant suspension was centrifuged. The supernatant was discarded and the precipitate resuspended in diethyl ether and centrifuged (2 times). The dark powder absorbed maximally at 638 nm in methanol solution.

EXAMPLE II

Preparation of Dye 8

The procedure described for the preparation of Dye 7 was followed, with the exception that 2,3-dimethylbenzothiazolium iodide was substituted for 3-ethyl-2-methylbenzothiazolium iodide in EXAMPLE I. The dye also had an absorption maximum at 638 nm in methanol.

EXAMPLE III

Preparation of Dye 9

The procedure described for the preparation of Dye 7 was followed, with the exception that 2,3-dimethylnaphthoxazolium iodide was substituted for 3-ethyl-2-methylbenzothiazolium iodide in EXAMPLE I. The dye had an absorption maximum of 624 nm in methanol.

EXAMPLE IV

Preparation of Dye 2

The procedure described for the preparation of Dye 7 was followed, with the exception that 3-fluoroaniline (1.84 g) was substituted for 3-chloroaniline in EXAMPLE I. The dye had an absorption maximum of 628 nm in methanol.

EXAMPLE V

Preparation of Dye 5

The procedure described for the preparation of Dye 7 was followed, with the exception that 3-bromoaniline (2.15 g) was substituted for 3-chloroaniline in EXAMPLE I. The dye had an absorption maximum at 638 nm in methanol.

EXAMPLE VI

Preparation of Dye 6

The procedure described for the preparation of Dye 7 was followed, with the exception that 1,1,2,3-tetramethyl-1H-benz(e)indolium iodide was substituted for 3-ethyl-2-methylbenzothiazolium iodide in EXAMPLE I. The dye had an absorption maximum at 623 nm in methanol.

EXAMPLE VII

Fluorescence was determined by dissolving the dye in a buffer ("CD4000 Retic Buffer") at neutral pH and at a final concentration of 0.5 μg/ml of test solution. The "CD4000 Retic Buffer" contained the following ingredients in the amounts indicated:

| Ingredient | Amount |
| --- | --- |
| Imidazole | 3.40 g |
| HCl, 1 N | 23.5 mL |
| NaCl | 6.80 g |
| "BIGCHAP" (N,N-bis[3-D-Gluconamidopropyl]cholamide) | 0.05 g |
| "PROCLIN 300" (mixture of 5-chloro-2-methyl-isothiazolone and 2-methyl-3(2H)-isothiazolone) | 0.315 g |
| Deionized water | to 1.0 liter |

The tests were run in a flow cytometer with a helium-neon laser light source. The helium-neon laser provided light at a wavelength of 630 nm. The optical system was a conventional optical system. The results are set forth in TABLE III.

TABLE III

| | Dye of U.S. Pat. No. 4,957,870 | Dye 2 | Dye 7 |
| --- | --- | --- | --- |
| Emission wavelength - dye only (nm) | 651.0 | 646.4 | 655.6 |
| Emission wavelength with RNA (nm) | 661.0 | 662.6 | 671.2 |
| Emission wavelength with DNA (nm) | 652.6 | 654.8 | 661.8 |
| Intensity - dye only | 1.0 | 1.0 | 1.0 |
| Enhancement with RNA | 55.10 | 91.80 | 39.1 |
| Enhancement with DNA | 54.10 | 76.10 | 50.4 |
| Bandwidth | 40 | | 45 |
| Bandwidth with RNA | 40 | | 36 |
| Bandwidth with DNA | 40 | | 35 |

From the data in TABLE III, it can be seen that Dye 10 of the present invention provide greater signal enhancement with DNA and with RNA than does the dye of U.S. Pat. No. 4,957,870.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method of detecting and enumerating reticulocytes in a test sample comprising the steps of:
   a. providing a test sample;
   b. adding to said test sample a dye having the formula:

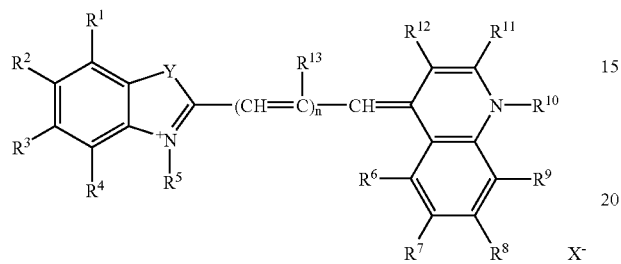

wherein:
   $R^1$, $R^2$, $R^3$, $R^4$ independently represent a member selected from the group consisting of hydrogen, halogen, aryl having more than one ring;
   $R^5$ represents an alkyl group having 1 to 6 carbon atoms or an aryl group having no more than one ring;
   $R^6$, $R^7$, $R^8$, $R^9$ independently represent a member selected from the group consisting of hydrogen, halogen, alkyl having 1 to 6 carbon atoms, aryl having no more than one ring, provided that at least one of $R^6$, $R^7$, $R^8$, $R^9$ represents halogen;
   $R^{10}$ represents an alkyl group having 1 to 6 carbon atoms or an aryl group having no more than one ring;
   $R^{11}$, $R^{12}$ independently represent a member selected from the group consisting of hydrogen, halogen, alkyl having 1 to 6 carbon atoms, aryl having no more than one ring;
   $R^{13}$ represents hydrogen or an alkyl group having 1 to 6 carbon atoms;
   Y represents S, O, C, or Se;
   n represents 1; and
   $X^-$ represents a counter ion, and
   c. measuring the fluorescence of said test sample to detect and enumerate reticulocytes in said test sample.

2. The method of claim 1, wherein said method of detecting and enumerating reticulocytes in a test sample is flow cytometry.

3. The method of claim 1, wherein said dye is selected from the group consisting of

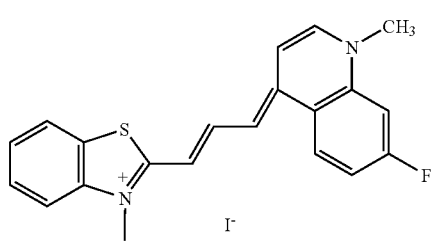

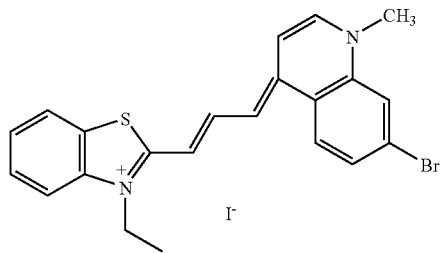

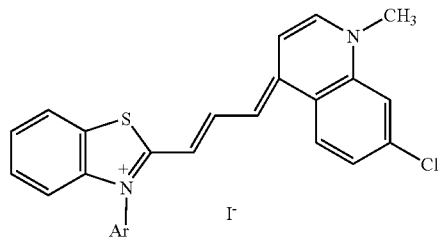

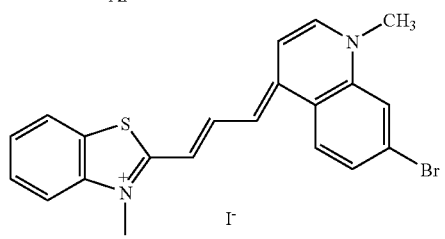

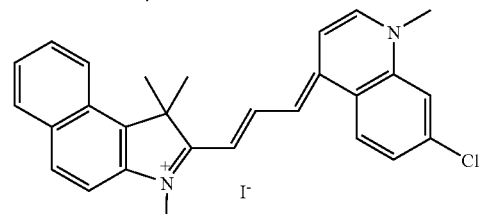

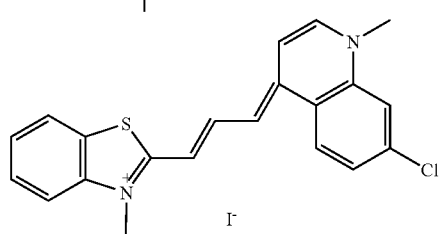

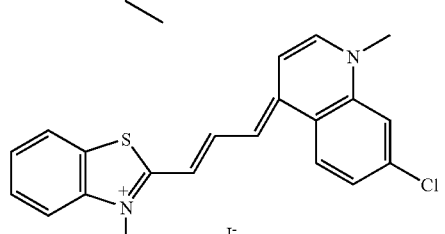

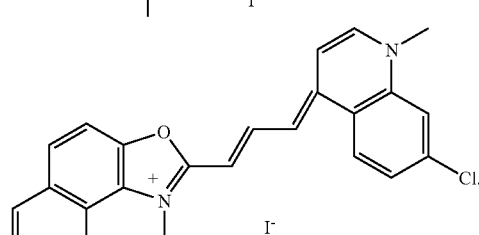

4. The method of claim 1, wherein said dye is not in the form of a conjugate.

5. A method of detecting cells in a test sample comprising the steps of:
   a. providing a test sample;
   b. adding to said test sample a conjugate comprising a dye having the formula:

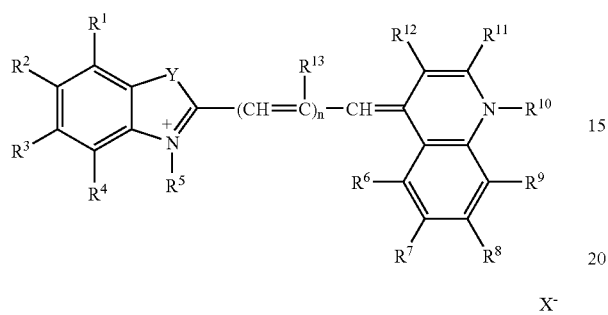

wherein:
   $R^1$, $R^2$, $R^3$, $R^4$ independently represent a member selected from the group consisting of hydrogen, halogen, aryl having more than one ring;
   $R^5$ represents an alkyl group having 1 to 6 carbon atoms or an aryl group having no more than one ring;
   $R^6$, $R^7$, $R^8$, $R^9$ independently represent a member selected from the group consisting of hydrogen, halogen, alkyl having 1 to 6 carbon atoms, aryl having no more than one ring, provided that at least one of $R^6$, $R^7$, $R^8$, $R^9$ represents halogen;
   $R^{10}$ represents an alkyl group having 1 to 6 carbon atoms or an aryl group having no more than one ring;
   $R^{11}$, $R^{12}$ independently represent a member selected from the group consisting of hydrogen, halogen, alkyl having 1 to 6 carbon atoms, aryl having no more than one ring;
   $R^{13}$ represents hydrogen or an alkyl group having 1 to 6 carbon atoms;
   Y represents S, O, C, or Se;
   n represents 1; and
   $X^-$ represents a counter ion, and
   c. measuring the fluorescence of said test sample to detect cells in said test sample.

6. The method of claim 5, wherein the cells are detected by a flow cytometer.

7. The method of claim 5, wherein said dye is selected from the group consisting of:

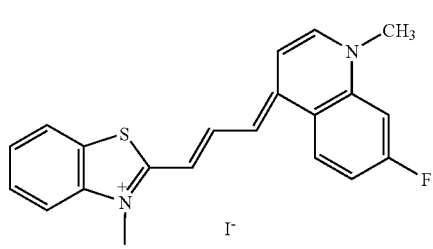

-continued

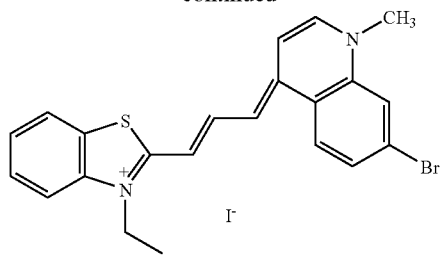

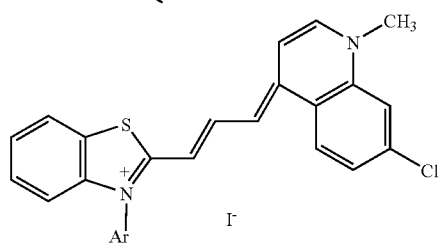

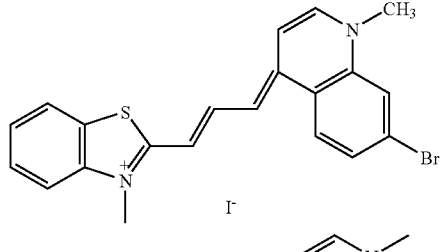

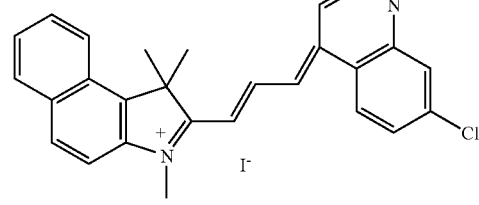

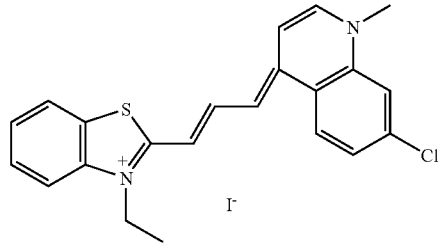

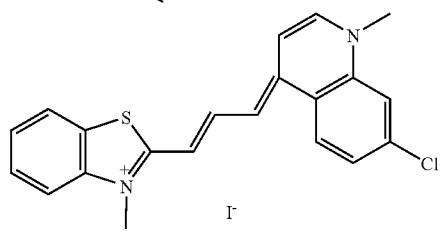

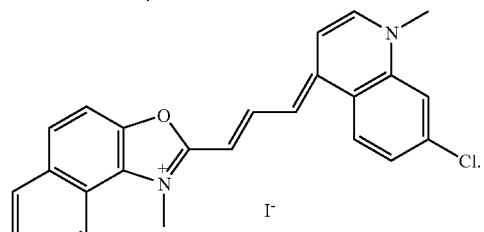

8. A method of performing a solid phase immunoassay, said method comprising the steps of:
   a. contacting a test sample suspected of containing an analyte with a capture reagent, whereby the analyte is bound to the capture reagent;
   b. treating the product of step a. with a conjugate, said conjugate comprising a binding member labeled with a dye having the formula:

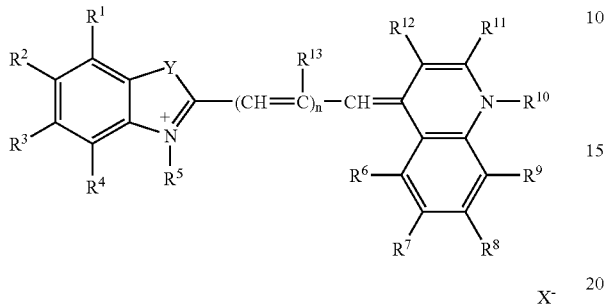

wherein:
   $R^1, R^2, R^3, R^4$ independently represent a member selected from the group consisting of hydrogen, halogen, aryl having more than one ring;
   $R^5$ represents an alkyl group having 1 to 6 carbon atoms or an aryl group having no more than one ring;
   $R^6, R^7, R^8, R^9$ independently represent a member selected from the group consisting of hydrogen, halogen, alkyl having 1 to 6 carbon atoms, aryl having no more than one ring, provided that at least one of $R^6, R^7, R^8, R^9$ represents halogen;
   $R^{10}$ represents an alkyl group having 1 to 6 carbon atoms or an aryl group having no more than one ring;
   $R^{11}, R^{12}$ independently represent a member selected from the group consisting of hydrogen, halogen, alkyl having 1 to 6 carbon atoms, aryl having no more than one ring;
   $R^{13}$ represents hydrogen or an alkyl group having 1 to 6 carbon atoms;
   Y represents S. O, C, or Se;
   n represents 1; and
   $X^-$ represents a counter ion, whereby the binding member of the conjugate becomes bound to the analyte to form a combination comprising the capture reagent, the analyte, and the conjugate;
   c. separating the combination formed in step b. from unbound conjugate;
   d. exciting the dye; and
   e. observing the signal generated by the dye to indicate the presence or amount of analyte in the test sample.

9. The method of claim 8, wherein the analyte is the product of an amplification reaction.

10. The method of claim 8, wherein said dye is selected from the group consisting of

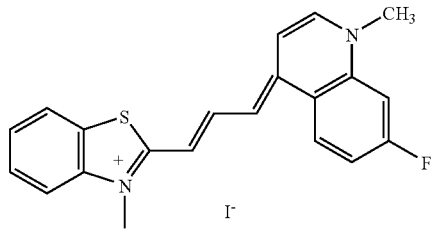

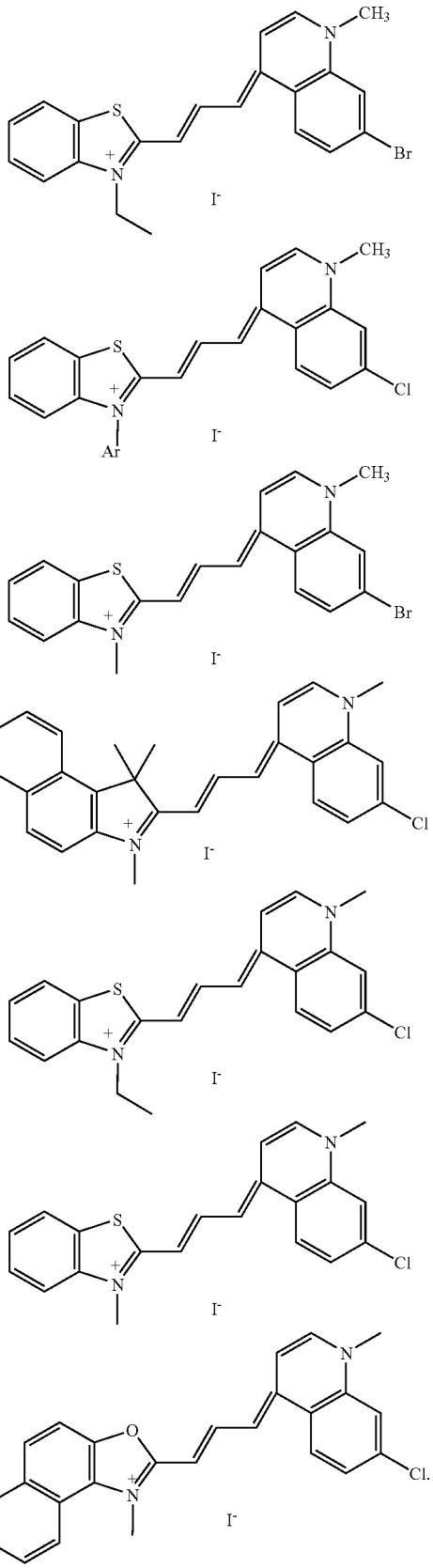

* * * * *

UNITED STATES PATENT AND TRADEMARK OFFICE
CERTIFICATE OF CORRECTION

| | | |
|---|---|---|
| PATENT NO. | : 7,083,982 B2 | Page 1 of 1 |
| APPLICATION NO. | : 10/288139 | |
| DATED | : August 1, 2006 | |
| INVENTOR(S) | : Nai-Yi Wang et al. | |

It is certified that error appears in the above-identified patent and that said Letters Patent is hereby corrected as shown below:

In Col. 19, line 42
replace "Y represents S. O, C, or Se;"
with --Y reprents S, O, C, or Se;--

Signed and Sealed this

Twenty-third Day of October, 2007

JON W. DUDAS
*Director of the United States Patent and Trademark Office*